(12) United States Patent
Ho

(10) Patent No.: US 9,447,064 B2
(45) Date of Patent: Sep. 20, 2016

(54) HETEROCYCLIC COMPOUND PREPARING

(71) Applicant: THE CHINESE UNIVERSITY OF HONG KONG, Hong Kong SAR (CN)

(72) Inventor: Chun Yu Ho, Laguna (CN)

(73) Assignee: THE CHINESE UNIVERSITY OF HONG KONG, Laguna, Hong Kong SAR (CN)

(*) Notice: Subject to any disclaimer, the term of this patent is extended or adjusted under 35 U.S.C. 154(b) by 0 days.

(21) Appl. No.: 14/266,342

(22) Filed: Apr. 30, 2014

(65) Prior Publication Data

US 2015/0315169 A1  Nov. 5, 2015

(51) Int. Cl.
| | |
|---|---|
| *C07D 309/18* | (2006.01) |
| *C07B 37/10* | (2006.01) |
| *C07D 313/04* | (2006.01) |
| *C07D 311/96* | (2006.01) |

(52) U.S. Cl.
CPC ............ *C07D 309/18* (2013.01); *C07B 37/10* (2013.01); *C07D 311/96* (2013.01); *C07D 313/04* (2013.01)

(58) Field of Classification Search
CPC  C07D 313/04; C07D 311/96; C07D 309/18; C07B 37/10
See application file for complete search history.

(56) References Cited

PUBLICATIONS

Song, Y-J., "Cationic NHC-Pd (NHC=N-heterocyclic carbene) complex-catalyzed cycloisomerization of dienes." Tetrahedron Letters 48.35 (2007): 6142-6146.*
Oxford English Dictionary 2015; accessed online Nov. 5, 2015 at http://www.oed.com/view/Entry/117270; p. 1-2.*
Ho, C-H.,"Medium-Sized Heterocycle Synthesis by the Use of Synergistic Effects of Ni-NHC and γ-Coordination in Cycloisomerization." The Journal of organic chemistry 79.24 (2014): 11873-11884.*
Kleinke, A.S., "Recent progress in the synthesis of oxepanes and medium ring ethers." Tetrahedron 68.35 (2012): 6999-7018.*
Song, Y-J.,"Cationic NHC-Pd (NHC=N-heterocyclic carbene) complex-catalyzed cycloisomerization of dienes." Tetrahedron Letters 48.35 (2007): 6142-6146.*
Ho, Chun-Yu et al., "Catalytic Intermolecular Tail-to-Tail Hydroalkenylation of Styrenes with α Olefins: Regioselective Migratory Insertion Controlled by a Nickel/N-Heterocyclic Carbene," Angew. Chem. Int. Ed., 2010, vol. 49, pp. 1982-1986.

* cited by examiner

*Primary Examiner* — Samantha Shterengarts
*Assistant Examiner* — Matt Mauro
(74) *Attorney, Agent, or Firm* — Ping Wang; Andrews Kurth LLP

(57) ABSTRACT

Disclosed is a process for selectively producing (D+1)-member heterocyclic compounds from corresponding unactivated dienes or derivatives thereof in the presence of a transition metal or lanthanide catalyst or a precursor thereof, relative to D-member heterocyclic rings.

8 Claims, 12 Drawing Sheets

| PEAK | V(F1) [ppm] | V(F1) [Hz] | INTENSITY [abs] |
|---|---|---|---|
| 1 | 7.2622 | 2905.8241 | 805436.17 |
| 2 | 6.7700 | 2708.8802 | 15276.60 |
| 3 | 5.3023 | 2121.6093 | 15508.48 |
| 4 | 4.7789 | 1912.1813 | 117337.64 |
| 5 | 4.7573 | 1903.5385 | 129526.59 |
| 6 | 4.1909 | 1676.9049 | 55785.25 |
| 7 | 4.1601 | 1664.5808 | 75102.52 |
| 8 | 3.9710 | 1588.9163 | 82568.80 |
| 9 | 3.9396 | 1576.3522 | 62531.97 |
| 10 | 3.7989 | 1520.0539 | 21128.57 |
| 11 | 3.7598 | 1504.4088 | 18810.48 |
| 12 | 3.3786 | 1351.8792 | 30760.29 |
| 13 | 3.3678 | 1347.5578 | 40803.22 |
| 14 | 3.3520 | 1341.2358 | 32858.90 |
| 15 | 2.4209 | 968.6747 | 32571.38 |
| 16 | 2.3919 | 957.0710 | 45595.06 |
| 17 | 2.3864 | 954.8703 | 49449.53 |
| 18 | 2.2887 | 915.7776 | 21892.92 |
| 19 | 2.2567 | 902.9734 | 33812.88 |
| 20 | 2.2257 | 890.5694 | 18012.58 |
| 21 | 1.7790 | 711.8313 | 34788.88 |
| 22 | 1.7731 | 709.4705 | 36226.83 |
| 23 | 1.7663 | 706.7496 | 34283.80 |
| 24 | 1.7465 | 698.8271 | 43292.17 |
| 25 | 1.7400 | 696.2262 | 43244.94 |
| 26 | 1.7342 | 693.9055 | 39627.66 |
| 27 | 1.5056 | 602.4357 | 47616.21 |
| 28 | 1.4795 | 591.9923 | 33976.96 |
| 29 | 1.4168 | 566.9042 | 93769.96 |
| 30 | 1.4017 | 560.8622 | 87013.93 |
| 31 | 1.3966 | 558.8216 | 94161.34 |
| 32 | 1.3688 | 547.6980 | 70572.91 |
| 33 | 1.3576 | 543.2165 | 71070.91 |
| 34 | 1.3365 | 534.7738 | 78341.47 |
| 35 | 1.3191 | 527.8115 | 104216.89 |
| 36 | 1.2928 | 517.2881 | 181203.81 |
| 37 | 1.2581 | 503.4036 | 92319.11 |
| 38 | 0.9898 | 396.0487 | 24243.96 |
| 39 | 0.9703 | 388.2461 | 15714.44 |
| 40 | 0.9023 | 361.0373 | 134535.78 |
| 41 | 0.8856 | 354.3551 | 275795.40 |
| 42 | 0.8682 | 347.3929 | 155614.46 |

HETEROCYCLIC COMPOUND PREPARING

FIELD

The present application relates to organic chemistry.

BACKGROUND

Heterocyclic compounds are often the key structures responsible for many natural products and pharmaceutical reagents biological activity. To synthesize derivatives, chemists well either start from the cyclic starting materials or from open chain linear structures followed by cyclization methods.

A number of catalyst systems are known for the preparations of cyclic compounds from combinations of unsaturated hydrocarbons, including olefins, alkynes and derivatives thereof. Representative cyclization methods using dienes including catalytic olefin ring closing metathesis and phosphorus/cyclopentyl group based/ligand free metal or lanthanide hydride or their derivatives catalyzed cyclization. These methods have been found to be extremely important in natural products/drug molecules syntheses, and fine chemical preparations. They both strongly favor the production of the smallest possible D-member rings (D=integer, via small molecules elimination or tail-to-tail cycloisomerization), but larger (D+1)-member rings are generally cannot be synthesized by these methods, except all-carbon linear cyclization precursors or specialized precursors with preformed cyclic back bones or under extreme Lewis acidity. Especially in case of an oxygen atom containing cyclization precursor is employed, those extreme Lewis acidity will lead to substrate decomposition or catalyst deactivation by means of unproductive chelations, and produce no desire (D+1)-member rings.

SUMMARY

In one aspect, the present application relates to a process for selectively producing (D+1)-member heterocyclic compounds from corresponding unactivated dienes or derivatives thereof in the presence of a metal catalyst or a precursor thereof, relative to D-member heterocyclic rings, wherein the metal catalyst represented by a general structure of [carbene$_L$MR$_L$]A$_L$ or a dimer or oligomers thereof, wherein M represents a transition metal or a lanthanide, A represents a leaving group, R represents a hydride or a carbon fragment, and L represents an integer wherein $1 \leq L \leq 4$.

BRIEF DESCRIPTION OF DRAWINGS

FIG. 7 is the $^1$H NMR spectra data of the product in Example 1.

DETAILED DESCRIPTION

Figure 1:
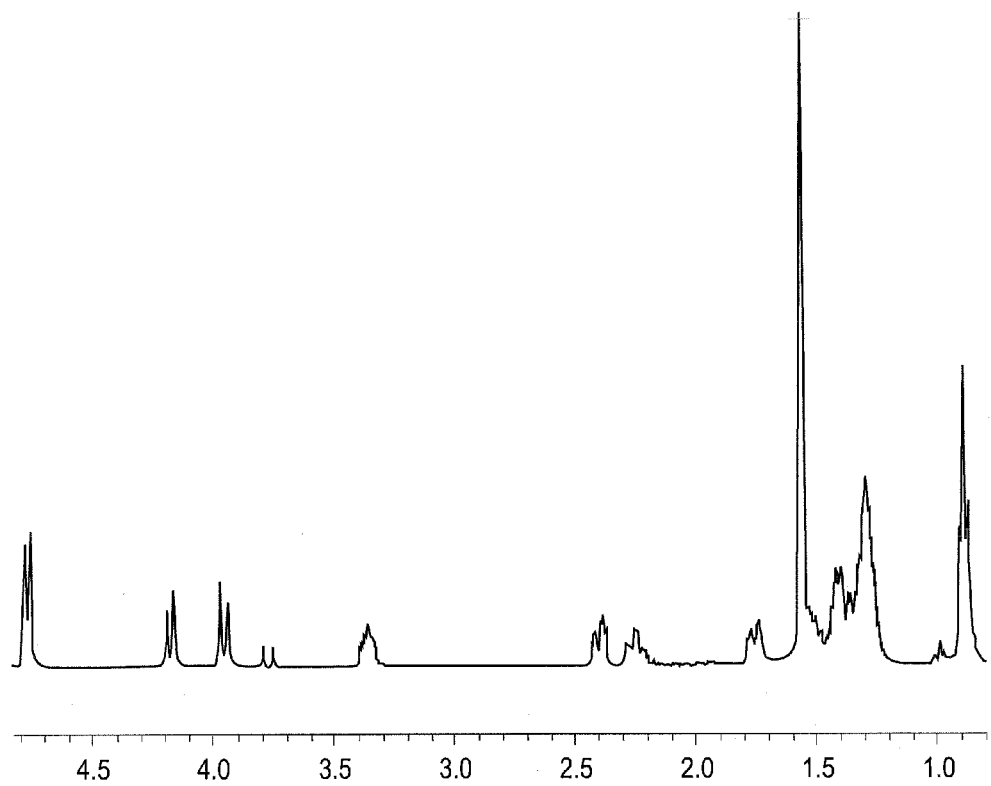
FIG. 1 is the $^1$H NMR spectra of the product in Example 1.

In the following description, certain specific details are included to provide a thorough understanding of various disclosed embodiments. One skilled in the relevant art, however, will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, which is as "including, but not limited to".

Reference throughout this specification to "one embodiment", or "an embodiment", or "in another embodiment", or "some embodiments", or "in some embodiments" means that a particular referent feature, structure, or characteristic described in connection with the embodiment is included in at least one embodiment. Thus, the appearance of the phrases "in one embodiment", or "in an embodiment", or "in another embodiment", or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a", "an", and "the" include plural referents unless the content clearly dictates otherwise. In this application, the use of "or" means "and/or" unless stated otherwise.

Certain chemical groups named herein are preceded by a shorthand notation indicating the total number of carbon atoms that are to be found in the indicated chemical group. For example, $C_7$-$C_{12}$ alkyl describes an alkyl group, as defined below, having a total of 7 to 12 carbon atoms, and $C_4$-$C_{12}$ cycloalkylalkyl describes a cycloalkylalkyl group, as defined below, having a total of 4 to 12 carbon atoms. The total number of carbons in the shorthand notation does not include carbons that may exist in substituents of the group described.

As used herein, "$C_m$ to $C_n$," or "$C_{m \text{ to } n}$" in which "m" and "n" are integers refers to the number of carbon atoms in an alkyl, alkenyl or alkynyl group or the number of carbon atoms in the ring of a cycloalkyl or cycloalkenyl group. That is, the alkyl, alkenyl, alkynyl, ring of the cycloalkyl or ring of the cycloalkenyl can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "m" and "n" are designated with regard to an alkyl, alkenyl, alkynyl, cycloalkyl or cycloalkenyl group, the broadest range described in these definitions is to be assumed.

DEFINITION

Unless defined otherwise, all technical and scientific terms used herein have the same meaning as is commonly understood by one of ordinary skill in the art to which this invention belongs. All patent, applications, published applications and other publications referenced herein are incorporated by reference in their entirety. In the event that there is plurality of definitions for a term herein, those in this section prevail unless stated otherwise.

The term "alkyl" as used herein alone or as part of a group means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —$SO_2$-substituted alkyl, —$SO_2$-aryl and —$SO_2$-heteroaryl.

Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The term "alkylene" as used herein alone or as part of a group refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like.

The term "cycloalkyl" as used herein alone or as part of a group refers to a completely saturated (no double bonds) mono- or multi-cyclic hydrocarbon ring system. When composed of two or more rings, the rings may be joined together in a fused, bridged or spiro-connected fashion. Cycloalkyl groups of this application may range from $C_3$ to $C_{10}$. In other embodiments, it may range from $C_3$ to $C_6$. A cycloalkyl group may be unsubstituted or substituted. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated.

The term "heterocyclic" as used herein alone or as part of a group is intended to mean three-, four-, five-, six-, seven-, and eight- or more membered rings wherein carbon atoms together with from 1 to 3 heteroatoms constitute the ring. A heterocyclic can optionally contain one or more unsaturated bonds situated in such a way, however, that an aromatic pi-electron system does not arise. The heteroatoms are independently selected from oxygen, sulfur, and nitrogen.

The term "aryl" as used herein alone or as part of a group is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl.

The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "transition metal" as used herein refers to any element in the d-block of the periodic table of the elements. This corresponds to groups 3 (IIIB) to 12 (IIB) on the periodic table.

The term "lanthanide" as used herein refers to any element in the f-block of the periodic table of the elements.

The term "ligand" in chemistry generally refers to an atom, ion, or molecule that bonds to a central metal, generally involving formal donation of one or more of its electrons. The metal-ligand bonding ranges from covalent to more ionic.

The term "carbene(s)" as used herein refers to an organic molecule containing a carbon atom with six valence electrons and having the general formula RR'C.

The term "optional" or "optionally" as used herein means that the subsequently described event of circumstances may or may not occur, and that the description includes instances where said event or circumstance occurs and instances in which it does not.

Unless otherwise indicated, when a substituent is deemed to be "optionally substituted", it is meant that the substituent is a group that may be substituted with one or more group(s) individually and independently selected from morpholinoalkanoate, cycloalkyl, aryl, heteroaryl, heterocyclyl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof.

For example, "optionally substituted aryl" means that the aryl radical may or may not be substituted and that the description includes both substituted aryl radicals and aryl radicals having no substitution.

Embodiments

In one aspect, the present application relates to a process for selectively producing (D+1)-member heterocyclic compounds from corresponding unactivated dienes or derivatives thereof in the presence of a metal catalyst or a precursor thereof, relative to D-member heterocyclic rings, wherein the metal catalyst represented by a general structure of $[carbene_L MR_L]A_L$ or a dimer or oligomers thereof, wherein M represents a transition metal or lanthanide catalyst, A represents a leaving group, R represents a hydride or a carbon fragment, and L represents an integer wherein $1 \leq L \leq 4$.

Exemplary carbene(s) or ligand(s) that can be used in the present application include, but are not limited to, heterocyclic carbenes, biscarbenes, bisheterocyclic carbenes, phosphines, amines, imines, arsines and derivatives thereof.

In some embodiments, the metal catalysts M can be a transition metal of group 9 or 10.

In some embodiments, A can be sulfonates.

In some embodiments, L can be equal to 1.

In some embodiments, the process is carried out with a metal-hydride catalyst.

In some embodiments, the process is carried out with ≤5 mol % of a metal-hydride catalyst.

In some embodiments, the D-member heterocyclic rings are obtained in olefin ring closing metathesis, phosphorus/cyclopentyl group based/ligand free metal or lanthanide hydride or their derivatives catalyzed cyclization, or acid catalyzed cycloisomerization.

In some embodiments, the (D+1)-member heterocyclic compounds contains one or more than one heteroatom.

Exemplary heteroatoms that can be used in the present application include, but are not limited to oxygen, nitrogen, sulfur, silicon, and metalloid atoms.

In some embodiments, the process is carried out in a solvent.

Exemplary solvents that can be used in the present application include, but are not limited to, aromatic hydrocarbons, aliphatic hydrocarbons, alicyclic hydrocarbons, halohydrocarbons, alcohols, ethers, esters, ketones, nitriles, diol derivatives, ionic liquids and supercritical liquid, such as supercritical $CO_2$.

In some embodiments, the process is carried out in a buffer.

Exemplary buffers that can be used in the present application include, but are not limited to, $NEt_3$, diisopropylethylamine, $K_2CO_3$ and $Cs_2CO_3$.

In some embodiments, the dienes or derivatives thereof are represented by the following formula

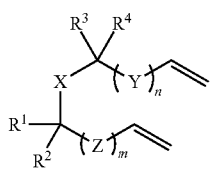

wherein $R^1$, $R^2$, $R^3$ and $R^4$ is independently selected from the group consisting of hydrogen, optionally substituted alkyl, optionally substituted aryl, and optionally substituted alkylene;

X is selected from the group consisting of oxygen, nitrogen, sulfur, silicon, and metalloid atoms;

Y and Z respectively represents a spacer and independently selected from the group consisting of optionally substituted alkyl, optionally substituted aryl, optionally substituted alkylene, an optionally substituted cycloalkyl, oxygen, nitrogen, sulfur, silicon, and metalloid atoms;

or one or more selected from the group consisting of $R^1$, $R^2$, $R^3$, $R^4$, X, Y and Z forms an optionally substituted linkers or a cycloalkyl;

n and m are each an integer respectively, wherein $0 \leq n \leq 50$, and $0 \leq m \leq 50$.

In some embodiments, the dienes or derivatives thereof are represented by the following formula

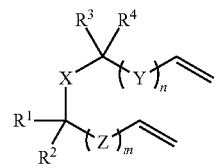

wherein $R^1$=n-pentyl, $R^2$=$R^3$=$R^4$=H, X=oxygen, n=0 and m=0.

In some embodiments, the dienes or derivatives thereof are represented by the following formula

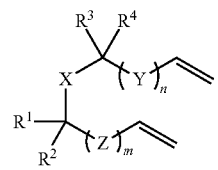

wherein $R^1$=$R^2$=$R^3$=H, $R^4$=phenyl, X=oxygen, n=1, m=0 and Y=$CH_2$.

In some embodiments, the (D+1)-member heterocyclic compounds are represented by the following formula

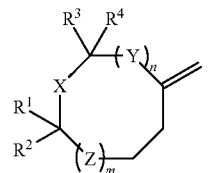

wherein $R^1$, $R^2$, $R^3$ and $R^4$ is independently selected from the group consisting of hydrogen, optionally substituted alkyl, optionally substituted aryl, and optionally substituted alkylene;

X is selected from the group consisting of oxygen, nitrogen, sulfur, silicon, and metalloid atoms;

Y and Z respectively represents a spacer and independently selected from the group consisting of optionally substituted alkyl, optionally substituted aryl, optionally substituted alkylene, an optionally substituted cycloalkyl, oxygen, nitrogen, sulfur, silicon, and metalloid atoms;

or one or more selected from the group consisting of $R^1$, $R^2$, $R^3$, $R^4$, X, Y and Z forms an optionally substituted linkers or a cycloalky;

n and m are each an integer respectively, wherein 0≤n≤50, and 0≤m≤50.

In some embodiments, the (D+1)-member heterocyclic compounds are represented by the following formula

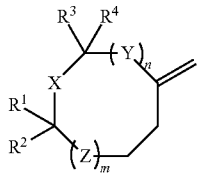

wherein $R^1$=n-pentyl, $R^2$=$R^3$=$R^4$=H, X=oxygen, n=0 and m=0.

the (D+1)-member heterocyclic compounds are represented by the following formula

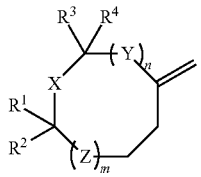

wherein $R^1$=$R^2$=$R^3$=H, $R^4$=phenyl, X=oxygen, n=1, m=0 and Y=$CH_2$.

In some embodiments, the process is carried out at room temperature.

In some embodiments, the process comprises adding a cyclization precursor to the medium containing an active catalyst at room temperature in one portion and stirring under inert atmosphere for 24 hrs.

In some embodiments, the resultant product is collected by filtering the crude reaction mixture using silica gel.

The process of the present application is able to provide (D+1)-member heterocyclic compounds catalytically over the D-member heterocyclic compounds typically observed in the other processes by simply using the same cyclization precursors, which also provides high functional group tolerance and without using stoichiometric amount of additives, leaving at least one synthetically versatile olefin (either exo- or endo-) intact for subsequent manipulations when necessary.

In addition, the cyclization is chemoselective in a sense which can differentiate the two olefin terminals, giving structural isomers contrasted to the other methods that can access.

The process of the present application may be useful as fragment coupling reactions in complex molecule synthesis.

The process of the present application is also environmentally friendly as it requires no stoichiometric amount of reagents/additives and produces no stoichiometric amount of waste, which provides the potential for large scale synthesis.

The process of the present application provides channels to facilitate the production of derivatives and intermediates complementary to the above existing technology, which permits a cost effective and rapid structure-activity relationship (SAR) studies or chemical library synthesis for pharmaceutical research and fine chemical preparations.

The (D+1)-member oxy heterocyclic compounds of the present application can be valuable products in chemical and pharmaceutical research, such as carbonyl compounds production by combined with conventional oxidation procedures and higher substituted alkenes by combined with olefin-cross metathesis technology.

The process for preparing the metal catalyst that can be used in the present application is well-known for one skilled in the art. For example, in some embodiments, the catalyst represented by a general structure of [carbene$_L$MR$_L$]A$_L$ or a dimer or oligomers thereof is prepared by reacting a metal with a carbene ligand and a R group.

In some embodiments, M can be a transition metal of group 9 or 10.

In some embodiments, A can be sulfonates.

In some embodiments, L can be equal to 1.

In some embodiments, the process for preparing the transition metal catalyst is carried out under non-acidic medium.

In some embodiments, the process for preparing the transition metal catalyst is carried out under buffered organic/ionic liquid medium.

The buffer may be used to minimize the problems related to isomerization, oligomerization and polymerization.

EXAMPLE

Embodiments of the present application are disclosed in further detail in the following examples, which are not in any way intended to limit the scope of the present invention.

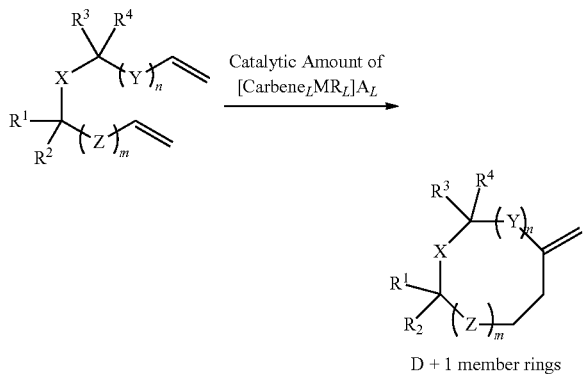

Site- Regio- & Chemo-Selective Cyclization Examples

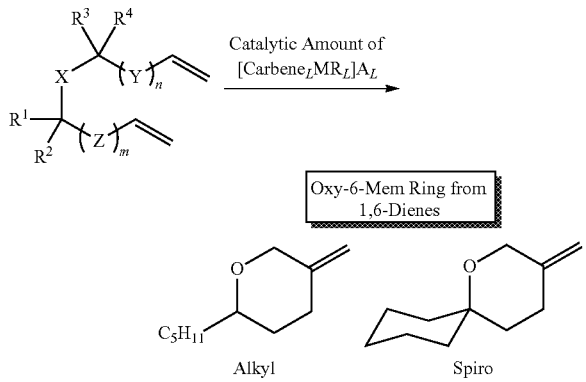

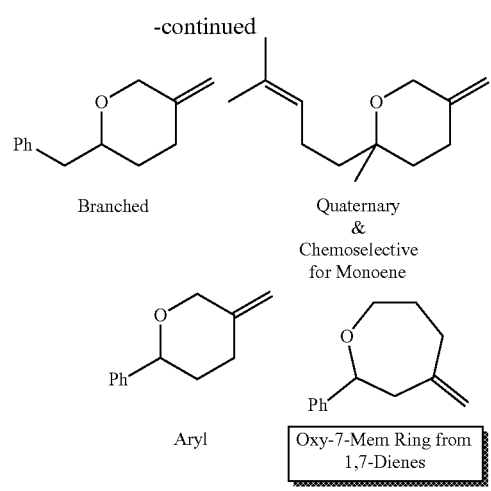

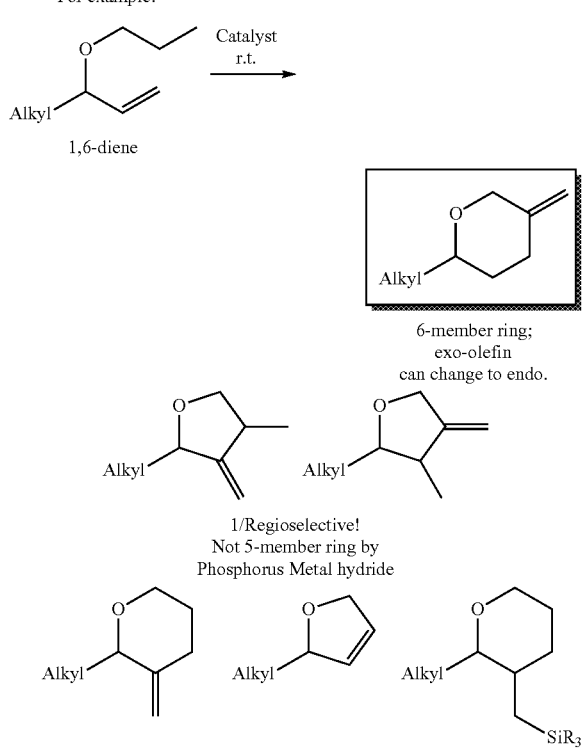

Higher substituted olefins and other substitution patterns including other heteroatoms can be used in the General Process.

The cyclization strongly favor the production of 6-member rings from 1,6-dienes, 7-member rings from 1,7-dienes, and the like, especially oxy heterocyclic compounds which have no successful example reported in the prior art. The cyclization is also highly chemoselective, providing structural isomers which are not accessible by current methods.

The catalyst with a general formula of [NHC—Ni—H]A (wherein A can be any halogen, sulfonates or other non-nucleophilic ions), [IPr—Ni—H]OTf as an example in this case, can be generated according to but not limited to the following literature procedure: "Catalytic Intermolecular Tail-to-Tail Hydroalkenylation of Styrenes with α Olefins: Regioselective Migratory Insertion Controlled by a Nickel/ N-Heterocyclic Carbene" Chun-Yu Ho, Lisi He, Angew. Chem. Int. Ed. 2010, 49, 9182. In some embodiments of the present application, the ligand "IPr" is 1,3-bis(2,6-di-iso-propylphenyl)imidazol-2-ylidene; CAS: 244187-81-3.

The [NHC—Ni—H]A species can be also generated by other methods, include but not limited to mixing a Ni source with 1) an imidazolium salt or an ionic liquid in general; or 2) alkyl, aryl, benzyl, vinyl, alkenyl or alkynyl A; or 3) a hydride or hydrogen source in general, optionally with the use of activators and buffers, this include but not limited to Lewis acidic additives, protic acid and or nucleophiles; or 4) other common organometallic transformations and manipulations techniques, such as hydride addition or elimination steps.

In some embodiments, the catalyst can be generated as follow: 1,3-bis(2,6-di-isopropylphenyl)imidazol-2-ylidene (IPr) (0.05 mmol) and Ni(cod)$_2$ (0.05 mmol) were added to an oven-dried test tube equipped with a stir bar in glove box. The tube was sealed with a septum, brought out of the glove box, and connected to a nitrogen line. The catalyst mixture was dissolved in degassed toluene (2 mL) under nitrogen and stirred at room temperature for 1 hour. The 1-octene (10 mol %), triethylamine (0.3 mmol), p-anisaldehyde (0.05 mmol, 5 mol %), triethylsilyltriflate (0.1 mmol, 10 mol %) were then added sequentially to the reaction mixture, and the mixture was stirred for 15 mins at rt.

Example 1

Figure 2:
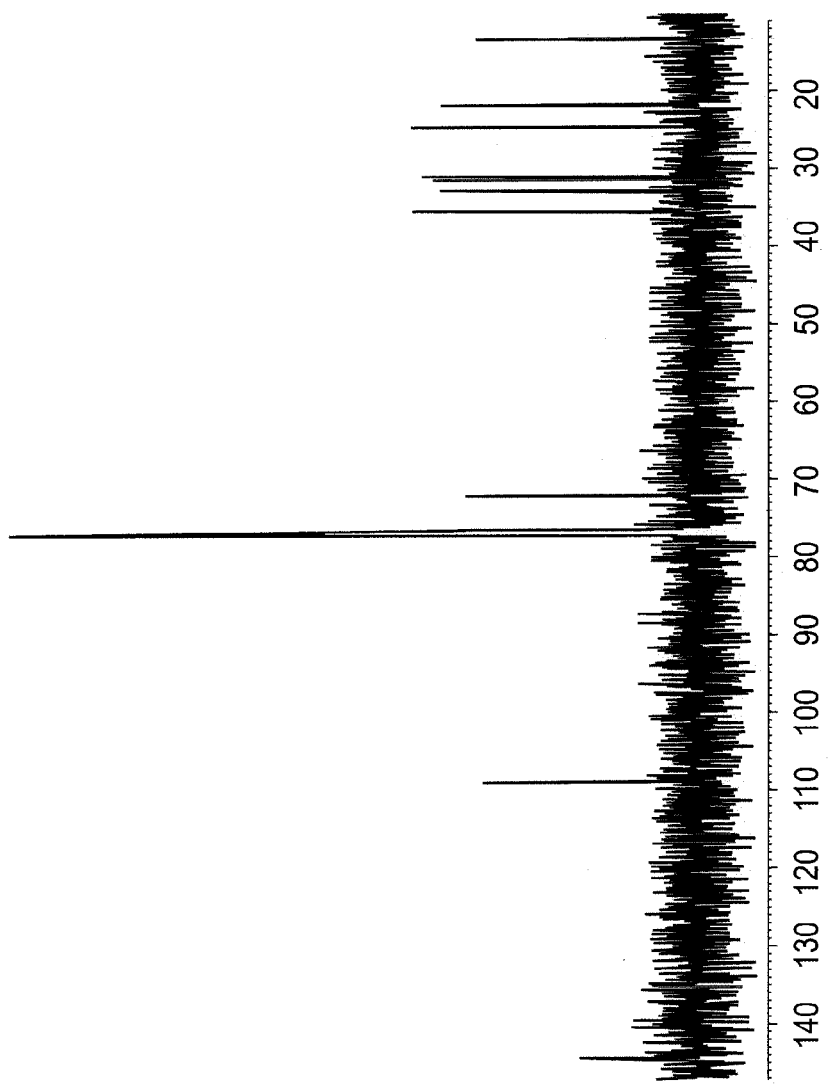
FIG. 2 is the $^{13}$C NMR spectra of the product in Example 1.
Figure 3:
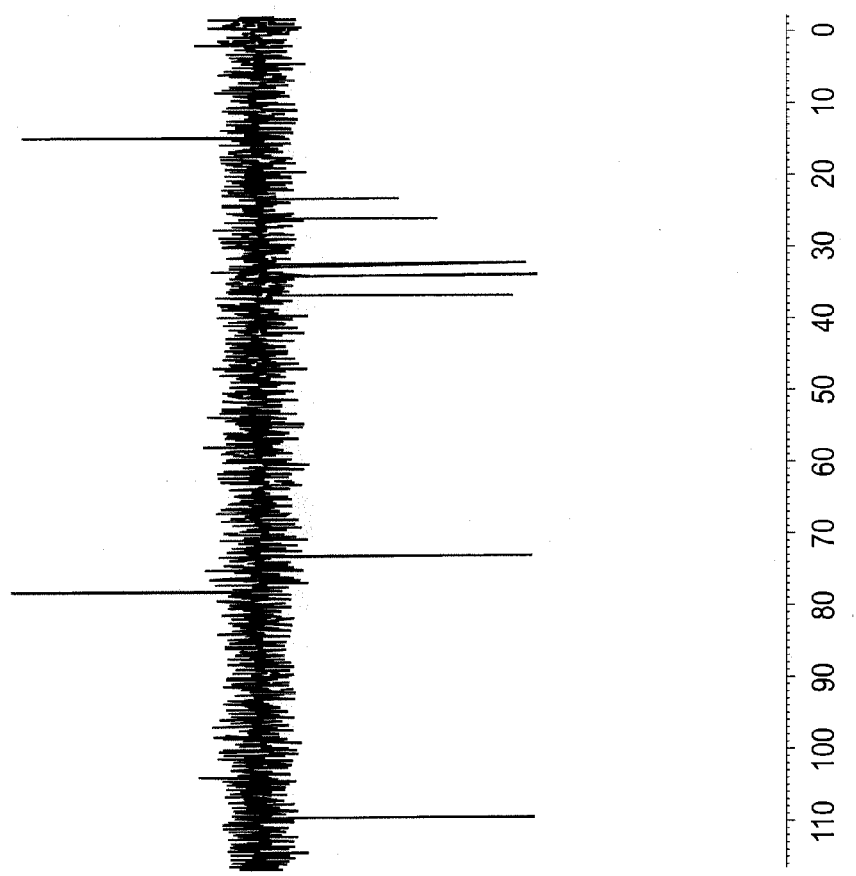
FIG. 3 is the $^{13}$C NMR spectra of the product in Example 1.
Figure 4:
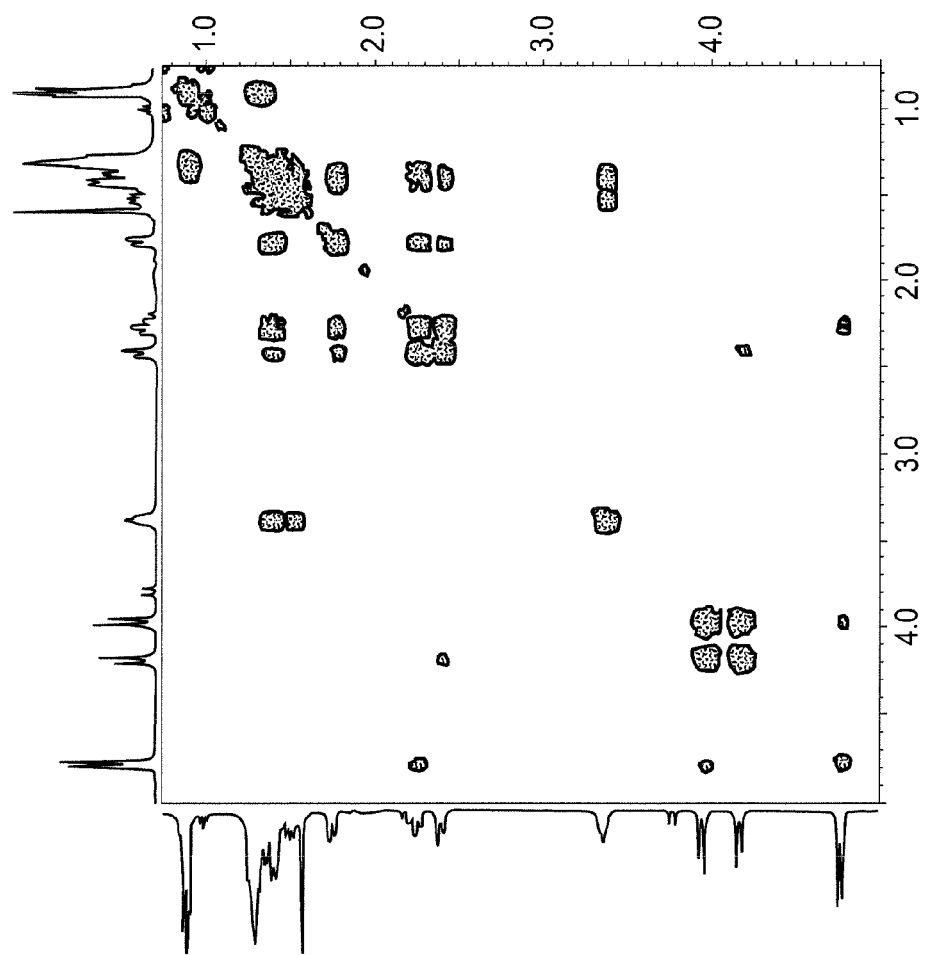
FIG. 4 is the COSY of the product in Example 1.
Figure 5:
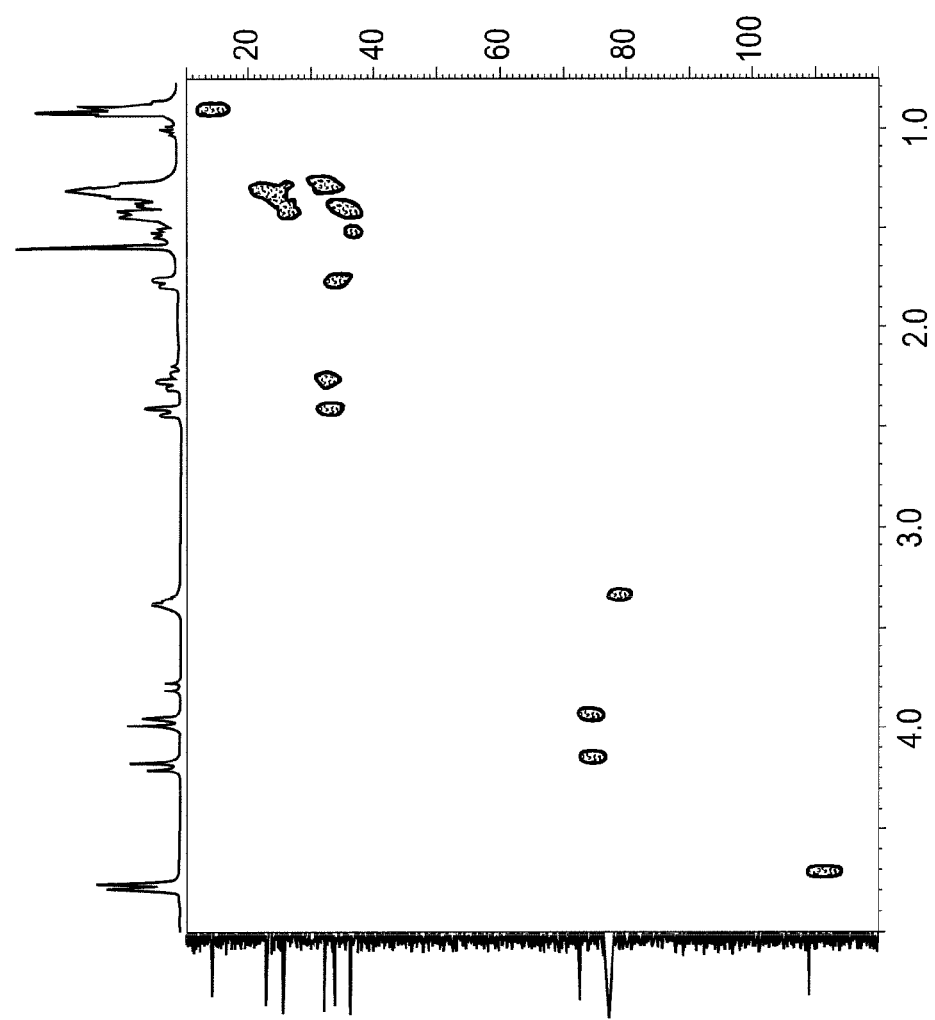
FIG. 5 is the HSQC of the product in Example 1.
Figure 6:
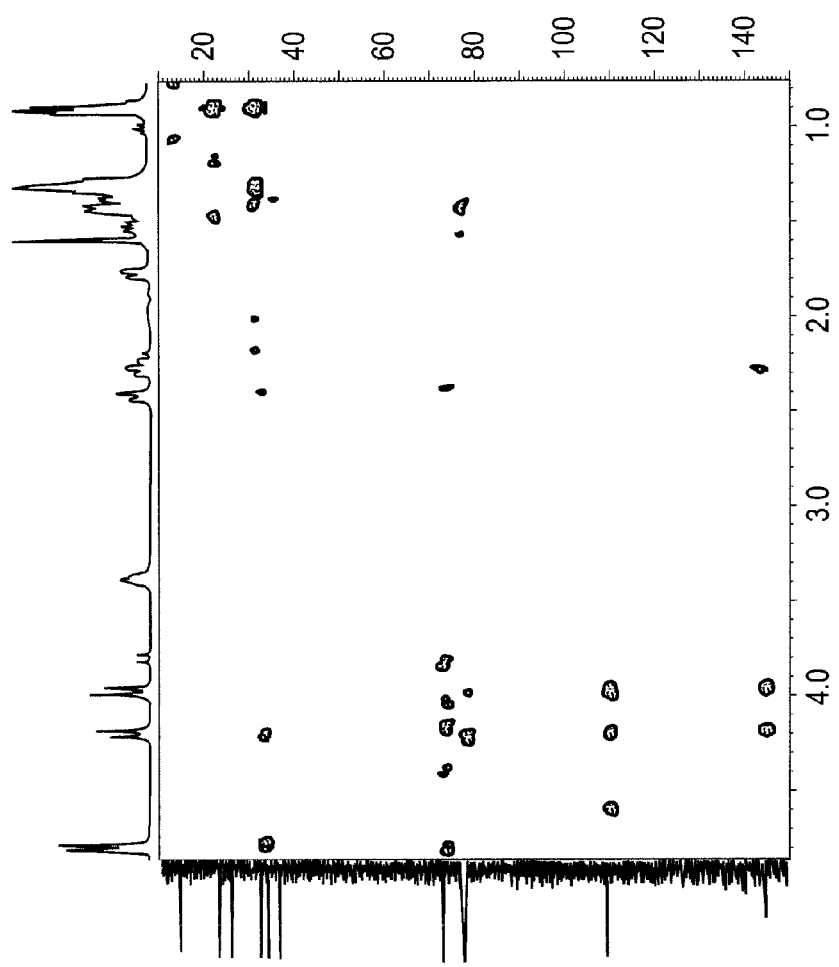
FIG. 6 is the HMBC of the product in Example 1.

In the instant example, the preparation conditions are identical to those described in the General Process, in which $R^1$=n-pentyl, $R^2$=$R^3$=$R^4$=H, X=oxygen, n=0 and m=0. The related spectra are provided in FIGS. 1 to 7. The 0.5 mmol cyclization precursor were added to the 0.05 mmol [IPr—Ni—H]OTf catalyst mixture at room temperature (10 mol % catalyst loading). The mixture was stirred 24 h at room temperature (23° C.). Then the mixture was added 10 mol % K$_2$CO$_3$, diluted with n-Hexane (4 mL) and was allowed to stir 30 mins in open air at room temperature. The mixture was then filtered through a short plug of silica gel and rinsed with 20% ethyl acetate/hexane (75 mL). The solvent was removed under reduced pressure, and purification via flash chromatography on silica gel afforded the desired cyclization product.

Example 2

Figure 8:
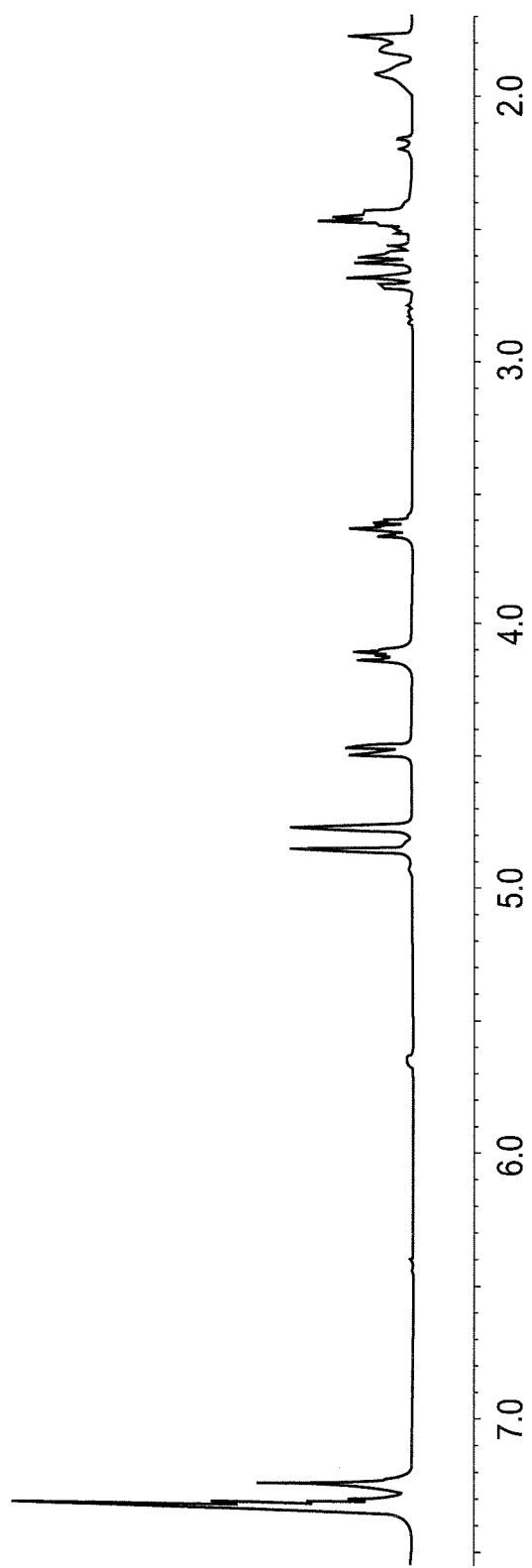
FIG. 8 is the $^1$H NMR spectra of the product in Example 2.
Figure 9:
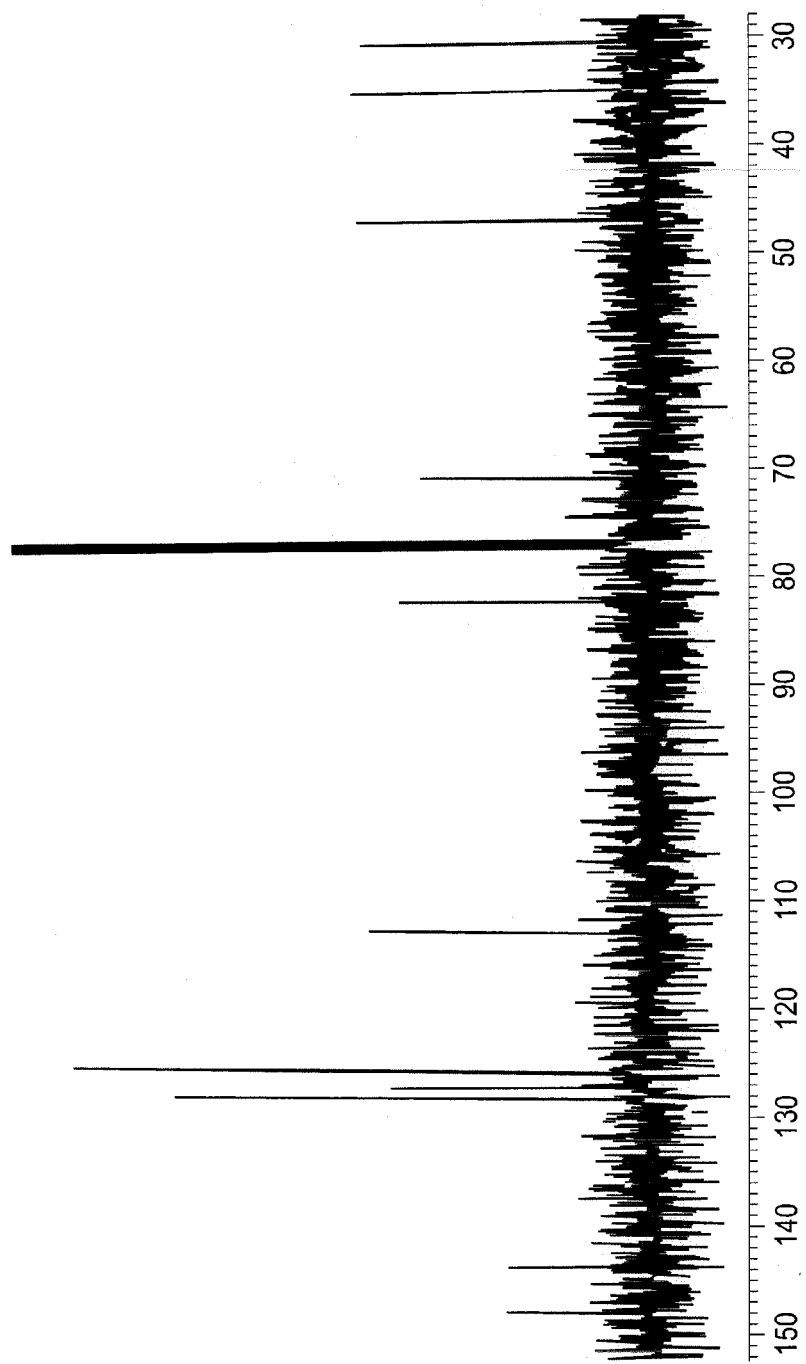
FIG. 9 is the $^{13}$C NMR spectra of the product in Example 2.
Figure 10:
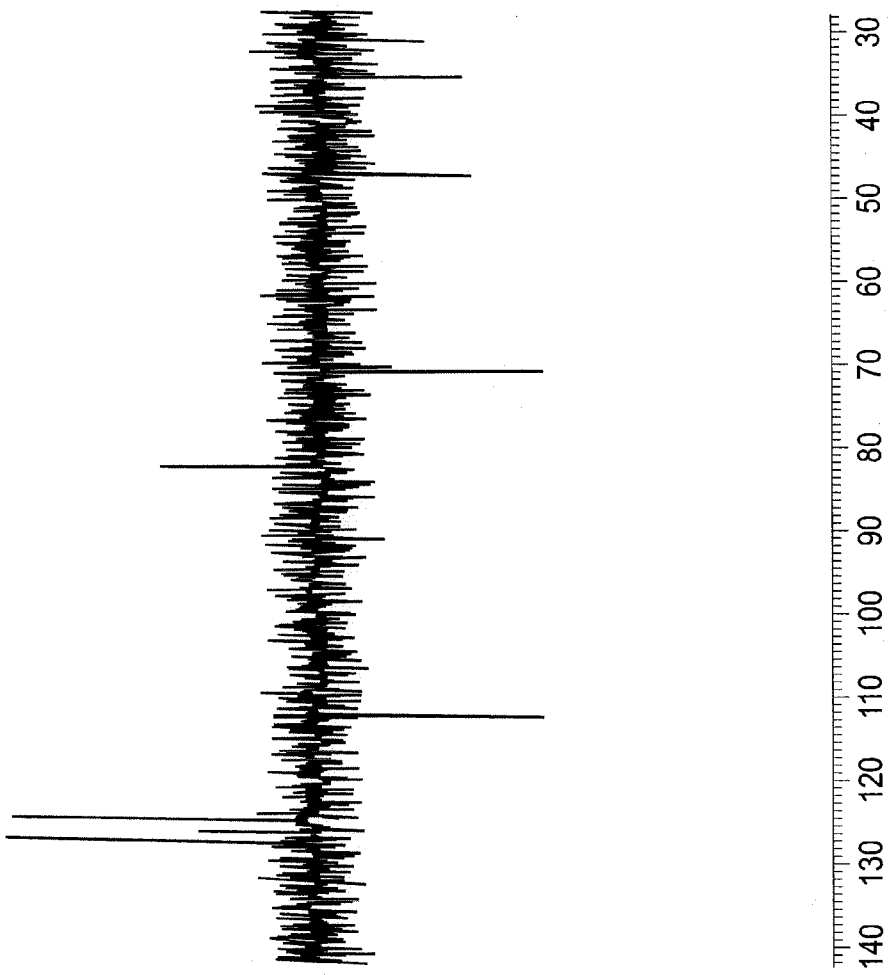
FIG. 10 is the $^{13}$C NMR spectra of the product in Example 2.
Figure 11:
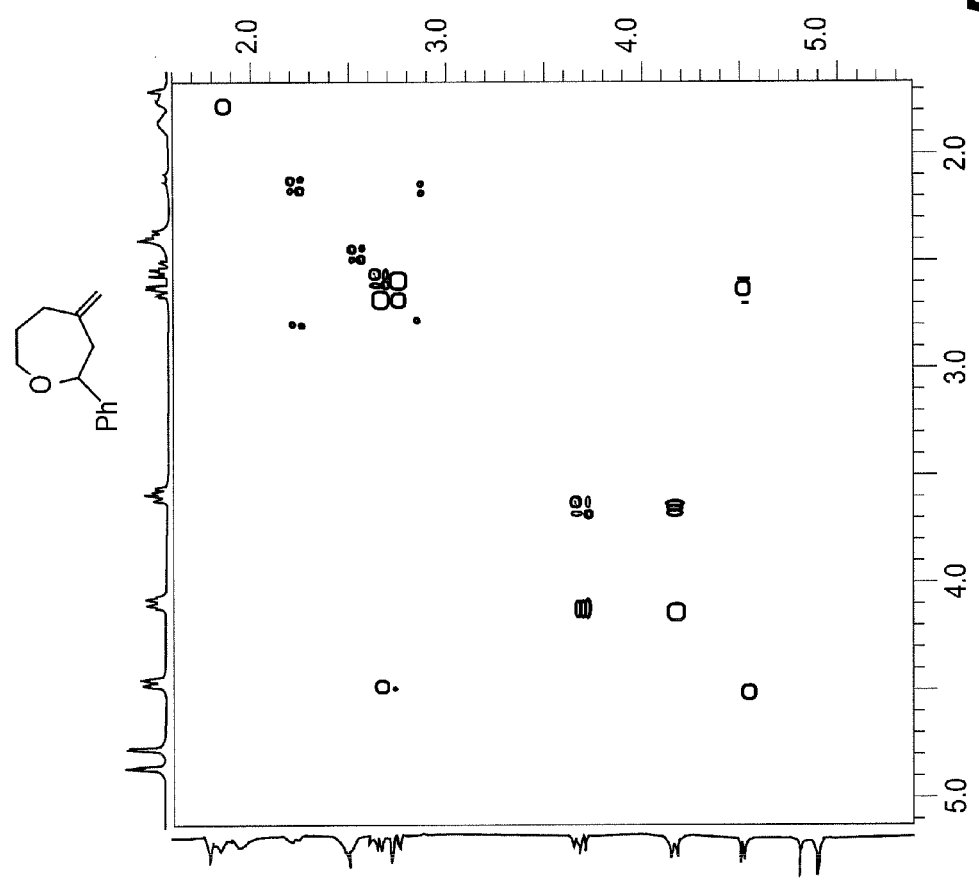
FIG. 11 is the COSY of the product in Example 2.
Figure 12:
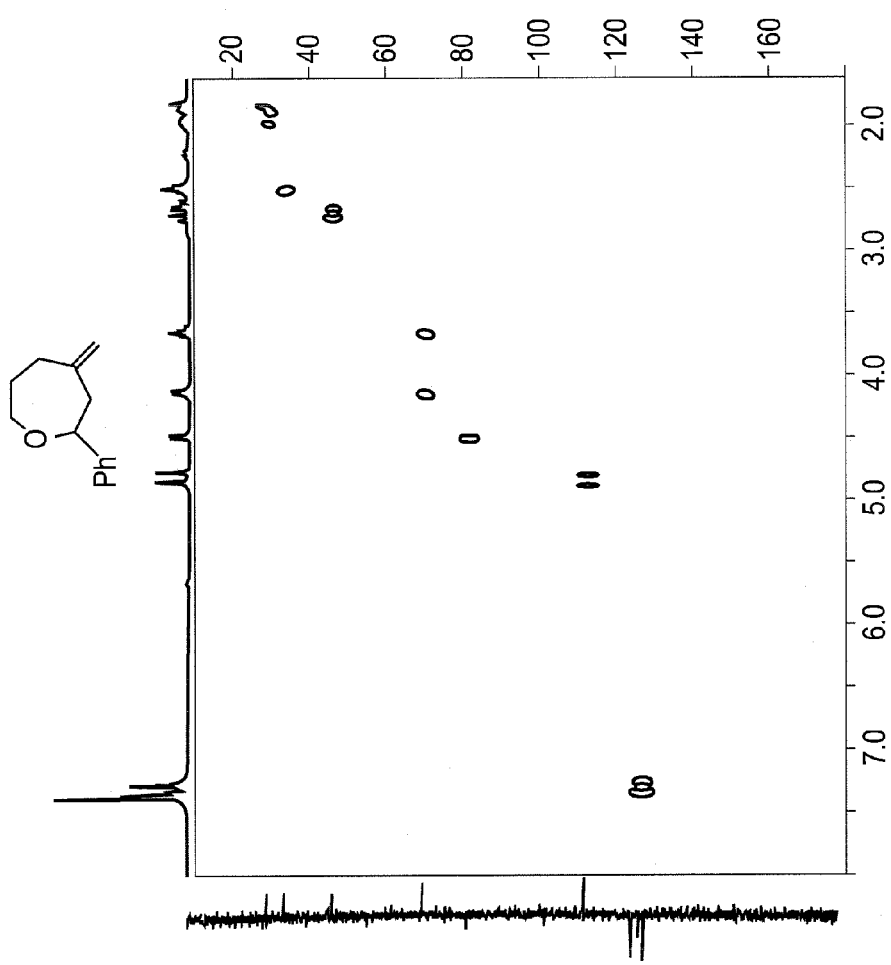
FIG. 12 is the HSQC of the product in Example 2.

In the instant example, the preparation conditions are identical to those described in the General Process, in which $R^1$=$R^2$=$R^3$=H, $R^4$=phenyl, X=oxygen, n=1, m=0 and Y=CH$_2$. The related spectra are provided in FIGS. 8 to 12. The 1.0 mmol cyclization precursor were added to the 0.05 mmol [IPr—Ni—H]OTf catalyst mixture at room temperature (5 mol % catalyst loading). The mixture was stirred 20 h at room temperature (23° C.). Then the mixture was added 10 mol % K$_2$CO$_3$, diluted with n-Hexane (4 mL) and was allowed to stir 30 mins in open air at room temperature. The mixture was then filtered through a short plug of silica gel and rinsed with 20% ethyl acetate/hexane (75 mL). The solvent was removed under reduced pressure, and purification via flash chromatography on silica gel afforded the desired cyclization product.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A process for selectively producing a heterocyclic compound from a diene in the presence of a buffer and a catalyst, wherein the catalyst is represented by the general structure [carbene$_L$MR$_L$]A$_L$, wherein M represents a transition metal selected from the group consisting of Fe, Co, Ni, Ru, Rh, Pd, Os, Ir, Pt, Cu, Ag, Au, Ti, Zr and Sc; R represents H or a carbon fragment; A represents a halogen, sulfonate or other non-nucleophilic ion; and L independently represents an integer wherein $1 \leq L \leq 4$;

the diene is represented by the formula

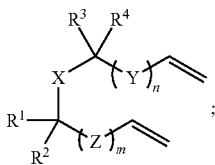

and the heterocyclic compound is represented by the formula

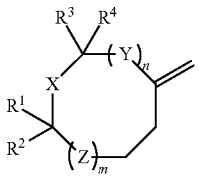

wherein $R^1$, $R^2$, $R^3$ and $R^4$ are independently selected from the group consisting of hydrogen, optionally substituted alkyl, optionally substituted aryl, and optionally substituted alkylene;

X is selected from the group consisting of oxygen, nitrogen, sulfur, and silicon;

Y and Z respective represent a spacer and are independently selected from the group consisting of optionally substituted alkyl, optionally substituted aryl, optionally substituted alkylene, an optionally substituted cycloalkyl, oxygen, nitrogen, sulfur, silicon, and metalloid atoms; or two or more members selected from the group consisting of $R^1$, $R^2$, $R^3$, $R^4$, X, Y and Z are linked; and n and m are each an integer respectively, wherein $0 \leq n \leq 50$, and $0 \leq m \leq 50$.

2. The process of claim 1, wherein the carbene is selected from the group consisting of heterocyclic carbenes, biscarbenes, and bisheterocyclic carbenes.

3. The process of claim 1, wherein the heterocyclic compound contains one or more than one heteroatom.

4. The process of claim 3, wherein the heteroatom is selected from the group consisting of oxygen, nitrogen, sulfur, silicon, and metalloid atoms.

5. The process of claim 1, wherein the process is carried out in a solvent.

6. The process of claim 5, wherein the solvent is selected from the group consisting of aromatic hydrocarbons, aliphatic hydrocarbons, alicyclic hydrocarbons, halohydrocarbons, alcohols, ethers, esters, ketones, nitriles, ionic liquids and supercritical fluids.

7. The process of claim 1, wherein $R^1$=n-pentyl, $R^2$=$R^3$=$R^4$=H, X=oxygen, n=0 and m=0.

8. The process of claim 1, wherein $R^1$=$R^2$=$R^3$=H, $R^4$=phenyl, X=oxygen, n=1, m=0 and Y=CH$_2$.

* * * * *